United States Patent [19]

Tolman et al.

[11] Patent Number: 4,755,516

[45] Date of Patent: Jul. 5, 1988

[54] ANTIVIRAL COMPOUNDS

[75] Inventors: Richard L. Tolman, Warren; Wallace T. Ashton, Clark, both of N.J.

[73] Assignee: Merck & Co., Inc., Rahway, N.J.

[21] Appl. No.: 35,127

[22] Filed: Apr. 6, 1987

Related U.S. Application Data

[63] Continuation-in-part of Ser. No. 644,095, Aug. 24, 1984, abandoned.

[51] Int. Cl.[4] .................... C07D 473/02; A61K 31/52
[52] U.S. Cl. .................................... 514/262; 514/263; 544/276; 544/277
[58] Field of Search ................ 514/263, 262; 544/277, 544/276

[56] References Cited

FOREIGN PATENT DOCUMENTS 0173624  3/1986  European Pat. Off. .

*Primary Examiner*—Nicholas S. Rizzo
*Attorney, Agent, or Firm*—Hesna J. Pfeiffer

[57] ABSTRACT 4-(Guanin-9-yl)butanals and their 3-oxa, 3-thia, and 2-ene counterparts and derivatives thereof, wherein the aldehyde is protected, which have antiviral activity, and are useful in treating viral infections, particularly herpes viral infections, such as herpes simplex viral infections, in mammals (especially humans), birds or fish.

8 Claims, No Drawings

ANTIVIRAL COMPOUNDS

This application is a continuation-in-part of U.S. patent application Ser. No. 644,095, filed Aug. 24, 1984, now abandoned.

The present invention relates to 4-(guanin-9-yl)butanals and their 3-oxa, 3-thia, and 2-ene counterparts and certain derivatives thereof where the aldehyde is protected, which have antiviral activity, and are useful in treating viral infections, particularly herpes viral infections, such as herpes simplex viral infections, in mammals (especially humans), birds or fish. The present invention also relates to methods of preparing these compounds.

The compounds of this invention may be represented by the formula:

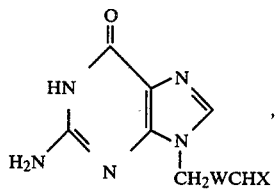
(I)

wherein
W is —OCH$_2$—, —CH$_2$CH$_2$—, —SCH$_2$— or —CH=CH—; and
X is

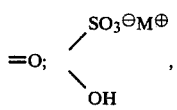

where M$^\oplus$ is a pharmaceutically-acceptable alkali metal cation, such as sodium or potassium; =NOR$^1$; =NR$^3$;

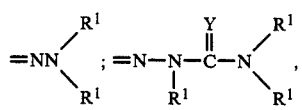

where Y is O, S or NH.HA, wherein HA is a pharmaceutically-acceptable inorganic or organic strong acid, such as hydrochloric acid, formic acid or phosphoric acid;

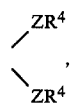

where each Z is independently O, S or NR$^1$, although preferably each Z is the same, and R$^4$ is selected from the definitions of R$^2$, or the two ZR$^4$ members taken together form a group

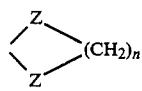

wherein n is 2 or 3;
each R$^1$ is independently hydrogen, alkyl having 1 to 6 carbon atoms, phenyl, phenyl substituted with halo (i.e., fluoro, chloro, bromo or iodo), with alkyl having 1 to 4 carbon atoms or with alkoxy having 1 to 4 carbon atoms, phenylalkyl wherein the alkyl moiety has 1 to 4 carbon atoms, or

each R$^2$ is independently alkyl having 1 to 6 carbon atoms, phenylalkyl wherein the alkyl moiety has 1 to 4 carbon atoms, phenyl, phenyl substituted with halo, with alkyl having 1 to 4 carbon atoms or with alkoxy having 1 to 4 carbon atoms;

each R$^3$ is independently selected from phenyl, phenyl substituted with halo, phenyl substituted with alkyl having 1 to 4 carbon atoms, phenyl substituted with alkoxy having 1 to 4 carbon atoms, piperidyl, furyl, imidazolyl, pyridyl, pyrimidyl and thienyl, and pharmaceutically-acceptable salts thereof.

Preferred compounds of the present invention are those wherein W is —OCH$_2$— or —CH$_2$CH$_2$— and X is as defined above.

More preferred compounds of the present invention are compounds of the formula I wherein
W is —OCH$_2$— or —CH$_2$CH$_2$;
X is

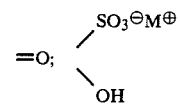

wherein M$^\oplus$ is a pharmaceutically acceptable alkali metal cation (e.g., sodium or potassium); =NOR$^1$; =NR$^3$;

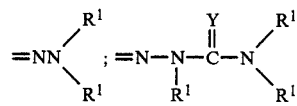

wherein Y is O or NH.HA, wherein HA is a pharmaceutically-acceptable inorganic or organic strong acid (e.g. hydrochloric acid, formic acid or phosphoric acid), and R$^1$ is hydrogen, methyl, or ethyl;

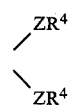

wherein each Z is independently O, S or NR$^1$ (preferably each Z is the same) and R$^4$ is R$^2$ or the two R$^4$s taken together with the Z moieties to which they are attached form a group

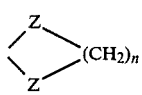

wherein n is 2 or 3;
each R$^1$ is independently hydrogen, alkyl having 1 to 6 carbon atoms, phenyl, phenyl substituted with halo, phenyl substituted with alkyl having 1 to 4 carbon atoms, phenyl substituted with alkoxy having 1 to 4 carbon atoms, phenylalkyl wherein the alkyl moiety has 1 to 4 carbon atoms, or

each $R^2$ is independently alkyl having 1 to 6 carbon atoms, phenylalkyl wherein the alkyl moiety has 1 to 4 carbon atoms, phenyl, phenyl substituted with halo, with alkyl having 1 to 4 carbon atoms or with alkoxy having 1 to 4 carbon atoms;

each $R^3$ is selected from phenyl, phenyl substituted with halo, phenyl substituted with alkyl having 1 to 4 carbon atoms, phenyl substituted with alkoxy having 1 to 4 carbon atoms, piperidyl, furyl, imidazolyl, pyridyl, pyrimidyl and thienyl.

Most preferred compounds of the present invention are compounds of the formula I wherein
W is —OCH$_2$— or —CH$_2$CH$_2$—;
X is

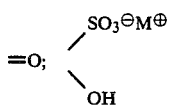

wherein $M^{\oplus}$ is a pharmaceutically-acceptable alkali metal cation (e.g., sodium or potassium); =NOR$^1$;

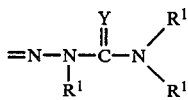

wherein Y is O or NH.HA wherein HA is a pharmaceutically-acceptable inorganic or organic strong acid (e.g. hydrochloric acid, formic acid or phosphoric acid);

wherein each Z is independently O or NR$^1$ (preferably each Z is the same) and R$^4$ is alkyl of 1 to 6 carbon atoms or alkoxyalkyl of 1 to 6 carbon atoms or the two R$^4$s taken together with the Z moieties to which they are attached form a group

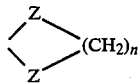

wherein Z is S, O, or NR$^1$ and n is 2 or 3;
each R$^1$ is independently hydrogen, alkyl having 1 to 6 carbon atoms, phenyl, phenyl substituted with halo (i.e., fluoro, chloro, bromo or iodo), phenyl substituted with alkyl having 1 to 4 carbon atoms, phenyl substituted with alkoxy having 1 to 4 carbon atoms, phenylalkyl wherein the alkyl moiety has 1 to 4 carbon atoms, or

each $R^2$ is independently alkyl having 1 to 6 carbon atoms, phenylalkyl wherein the alkyl moiety has 1 to 4 carbon atoms, phenyl or phenyl substituted with halo, with alkyl having 1 to 4 carbon atoms or with alkoxy having 1 to 4 carbon atoms;

each $R^3$ is selected from phenyl, phenyl substituted with halo, phenyl substituted with alkyl having 1 to 4 carbon atoms, phenyl substituted with alkoxy having 1 to 4 carbon atoms, piperidyl, furyl, imidazolyl, pyridyl, pyrimidyl and thienyl.

The pharmaceutically-acceptable salts of the compounds of the instant invention include the conventional soluble, non-toxic salts of these compounds, for example, from non-toxic inorganic or organic acids and/or with metal salts, such as those of sodium, potassium, or lithium. Some of the conventional salts include those derived from inorganic acids, such as hydrochloric, hydrobromic, sulfuric, sulfamic, phosphoric or nitric, or from organic acids, such as ethane disulfonic, trifluoroacetic, isethionic, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, and the like.

The butanals of the formula I may all be prepared by alkylation of the appropriate guanine or protected guanine (e.g. as the trimethylsilyl derivative) with the desired alkyl, oxaalkyl, thiaalkyl, or alkenyl side chain containing a vicinal diol at the 4- and 5- carbons. After deprotection of the guanine, treatment with periodate cleaves the diol to produce the corresponding butanal.

4-(Guanin-9-yl)-3-oxabutanal is prepared by treatment of an aqueous suspension of 9-(2,3-dihydroxy-1-propoxymethyl)guanine with sodium periodate at ambient temperature. Alternatively, it may be prepared by oxidation of 9-(2-hydroxyethoxymethyl)guanine (acyclovir) using, e.g., Pfitzner-Moffatt-type conditions, such as treatment at room temperature with N,N'-dicyclohexylcarbodiimide, dichloroacetic acid, and dimethylsulfoxide (DMSO). Derivatives are prepared by reaction of 4-(guanin-9-yl)-3-oxabutanal with the appropriate reagent, such as sodium bisulfite, potassium bisulfite, hydroxylamine, a hydrazine or hydrazide, an aryl or heterocyclic amine or diamine, an alcohol, diol, thiol or dithiol in a suitable solvent, e.g., water, acetic acid, dimethylformamide (DMF), or DMSO, at temperatures of about 0°–150° C. The reaction may be conducted in the presence of a base or buffer, and if necessary a catalyst like boron trifluoride etherate or p-toluenesulfonic acid may be added. Pharmaceutically acceptable salts of compounds of the present invention may be prepared using standard techniques. For example, a salt may be formed at the purine ring by dissolving the compound in water with one equivalent of sodium hydroxide and then lyophilizing.

The preparation of 9-(2,3-dihydroxy-1-propoxymethyl)guanine, used as a starting material, is disclosed in European Patent Application No. 82401571.3, published Aug. 24, 1982 (Publication No. 0 074 306).

The following compounds are representative of the compounds of the present invention:
4-(guanin-9-yl)-3-oxabutanal;
4-(guanin-9-yl)-3-oxabutanal oxime;

9-(2-hydroxy-2-sulfoethoxymethyl)guanine, sodium salt;
9-[2,2-(N,N'-diphenylethylenediamino)ethoxymethyl]guanine;
4-(guanin-9-yl)-3-oxabutanal semicarbazone;
4-(guanin-9-yl)-3-oxabutanal thiosemicarbazone;
4-(guanin-9-yl)-3-oxabutanal guanylhydrazone hydrochloride;
4-(guanin-9-yl)-3-oxabutanal phenylhydrazone;
9-[2-(m-methoxyphenylimino)ethoxymethyl]]guanine;
9-[2-(1,3-dioxolan-2-yl)methoxymethyl]]guanine;
9-[2-(1,3-dithian-2-yl)methoxymethyl]]guanine;
4-(guanin-9-yl)butanal;
4-(guanin-9-yl)but-2-enal;
4-(guanin-9-yl)-3-thiabutanal;
4-(guanin-9-yl)-3-thiabutanal oxime;
4-(guanin-9-yl)butanal oxime; and
4-(guanin-9-yl)but-2-enal oxime.

The following compounds are preferred:
4-(guanin-9-yl)-3-oxabutanal;
4-(guanin-9-yl)-3-oxabutanal oxime;
9-(2-hydroxy-2-sulfoethoxymethyl)guanine, sodium salt;
9-[2,2-(N,N'-diphenylethylenediamino)ethoxymethyl]guanine;
4-(guanin-9-yl)-3-oxabutanal semicarbazone;
4-(guanin-9-yl)-3-oxabutanal thiosemicarbazone;
4-(guanin-9-yl)-3-oxabutanal guanylhydrazone hydrochloride;
4-(guanin-9-yl)-3-oxabutanal phenylhydrazone;
4-(guanin-9-yl)butanal;
4-(guanin-9-yl)but-2-enal;
4-(guanin-9-yl)-3-thiabutanal;
4-(guanin-9-yl)-3-thiabutanal oxime;
4-(guanin-9-yl)butanal oxime; and
4-(guanin-9-yl)but-2-enal oxime.

The following compounds are particularly preferred:
4-(guanin-9-yl)-3-oxabutanal;
4-(guanin-9-yl)-3-oxabutanal oxime;
9-(2-hydroxy-2-sulfoethoxymethyl)guanine, sodium salt;
4-(guanin-9-yl)butanal; and
9-[2,2-(N,N'-diphenylethylenediamino)ethoxymethyl]guanine.

In another aspect of the invention, there is provided a pharmaceutical composition or preparation comprising a compound of formula I wherein X is as hereinbefore defined; or a pharmaceutically-acceptable salt thereof; together with a pharmaceutically-acceptable carrier therefor. In a particular aspect, the pharmaceutical composition comprises a compound of formula (I) in effective unit dosage form.

As used herein the term "effective unit dosage" or "effective unit dose" is denoted to mean a predetermined antiviral amount sufficient to be therapeutically-effective in vivo against a virus in mammals (especially humans), birds or fish.

In Kinahan et al., *Cancer Research*, 40, 598–603 (1980) and Kaufman et al., *Cancer Chemotherapy Reports*, Part 1, Vol. 59, No. 5, 1007–1014, Sept./Oct. 1975, purine and pyrimidine dialdehydes, similar to the compounds of the instant invention, are shown to be effective chemotherapeutic agents in antitumor applications, thus also suggesting that the instant compounds may possess useful cytotoxic behavior against some forms of neoplastic disease treatable by such anticancer agents.

Pharmaceutically-acceptable carriers are materials useful for the purpose of administering the medicament, and may be solid, liquid or gaseous materials, which are otherwise inert and medically-acceptable and are compatible with the active ingredients.

These pharmaceutical compositions may be given parenterally, orally, used as a suppository or pessary, applied topically as an ointment, cream, aerosol, or powder, or given as eye or nose drops, etc., depending on whether the preparation is used to treat internal or external viral infections or on the nature of the tumor to be treated.

The compounds of formula I may also be combined in appropriate formulations, with other antiviral or other cancer chemotherapeutic agents.

For internal infections or in chemotherapy the compositions are administered orally or parenterally at dose levels, calculated as the free base, of about 0.1 to 250 mg per kg, preferably 1.0 to 50 mg per kg of mammal body weight, and are used in humans in a unit dosage form, administered, e.g., one or more times daily, in the amount of 1 to 250 mg per unit dose.

For oral administration, fine powders or granules may contain diluting, dispersing and/or surface active agents, and may be presented in a draught, in water or in a syrup; in capsules or sachets in the dry state or in a non-aqueous solution or suspension, wherein suspending agents may be included; in tablets, wherein binders and lubricants may be included; or in a suspension in water or a syrup. Where desirable or necessary, flavoring, preserving, suspending, thickening or emulsifying agents may be included. Tablets and granules are preferred, and these may be coated.

For parenteral administration or for administration as drops, as for eye infections, the compounds may be presented in aqueous solution in a concentration of from about 0.1 to 10% more preferably 0.1 to 7%, most preferably 0.2% w/v. The solution may contain antioxidants, buffers, etc.

Alternatively for infections of the eye, or other external tissues, e.g., mouth and skin, the compositions are preferably applied to the infected part of the body of the patient as a topical ointment or cream. The compounds may be presented in an ointment, for instance, with a water soluble ointment base, or in a cream, for instance with an oil in water cream base, in a concentration of from about 0.1 to 10%, preferably 0.1 to 7%, most preferably 1% w/v.

The following non-limiting Examples illustrate the preparation of representative compounds and compositions of the present invention. All temperatures are in °C.

EXAMPLE 1

4-(Guanin-9-yl)-3-oxabutanal

To a vigorously stirred solution of 1.42 g (6.66 mmole) of sodium periodate in 14 ml of water at room temperature was added 1.34 g (5 mmole) of 9-(2,3-dihydroxy-1-propoxymethyl)guanine. The addition was accompanied by a mild exotherm. The reaction flask was stoppered, and stirring was continued at ambient temperature. After 1.5 hours, by which time the reaction was judged to be complete by high pressure liquid chromatography, the mixture was filtered. The solid on the filter was washed with small volumes of cold water and then with acetone. After air-drying overnight, yield of white powder was 1.13 g (90%), m.p. 350° (darkened beginning at about 250° without melting). Satisfactory purity was confirmed by TLC (80:20:2 $CHCl_3$- methanol-H$_2$O) and analytical high pressure liquid chromatography (H$_2$O, C$_8$ reverse phase). By NMR (DMSO-d$_6$) the material existed as a mixture of free aldehyde and covalent hydrate in a ratio of approximately 1:3 (This ratio was variable in different preparations).

| Anal. (C$_8$H$_9$N$_5$O$_3$ 1.5 H$_2$O) | | |
|---|---|---|
| | Calculated | Found[a] |
| C | 38.40 | 38.54 |
| H | 4.84 | 4.60 |
| N | 27.99 | 27.71 |

[a] For sample recrystallized from water

EXAMPLE 2

9-[2,2-(N,N'-Diphenylethylenediamino)ethoxymethyl]-guanine

A mixture of 250 mg (1 mmole) of hydrated 4-(guanin-9-yl)-3-oxabutanal 249 mg (1 mmole) of 85% N,N'-diphenylethylenediamine, and 2 ml of glacial acetic acid was heated on a steam bath. All of the solid dissolved rapidly on warming, but heavy precipitation of product soon occurred. After 5 minutes, the mixture was cooled and diluted with 6 ml of methanol. The solid was collected on a filter and washed with methanol to give, after air drying, 367 mg (87%) of nearly white crystals, m.p. 273°–274° dec. Structure and purity were confirmed by NMR (DMSO-d$_6$) and TLC (thin layer chromatography) (9:1 CHCl$_3$-methanol).

| Anal. (C$_{22}$H$_{23}$N$_7$O$_2$ 0.2 H$_2$O) | | |
|---|---|---|
| | Calculated | Found |
| C | 62.75 | 62.82 |
| H | 5.60 | 5.49 |
| N | 23.29 | 23.13 |

EXAMPLE 3

4-(Guanin-9-yl)-3-oxabutanal oxime

A mixture of 50 mg (0.2 mmole) of hydrated 4-(guanin-9-yl)-3-oxabutanal, 17.5 mg (0.25 mmole) of hydroxylamine hydrochloride, and 0.5 ml of water was stirred vigorously at room temperature as 0.18 ml (0.45 mmole) of 2.5N sodium hydroxide was added dropwise. After about 5 minutes the mixture was diluted with an additional 0.5 ml of water. After 3 hours the mixture was made weakly acidic by addition of glacial acetic acid. The solid was collected on a filter, washed with water, and air dried to give 33 mg (69%) of white solid, m.p. 248°–250° dec. Structure and satisfactory purity were confirmed by NMR (DMSO-d$_6$), thin layer chromatography (80:20:2 CHCl$_3$-methanol-H$_2$O), and analytical high pressure liquid chromatography (C$_8$ reverse phase, 95:5 H$_2$O-methanol).

| Anal. (C$_8$H$_{10}$N$_6$O$_3$ 0.1 H$_2$O) | | |
|---|---|---|
| | Calculated | Found |
| C | 40.03 | 39.83 |
| H | 4.28 | 4.18 |
| N | 35.02 | 35.03 |

EXAMPLE 4

9-(2-Hydroxy-2-sulfoethoxymethyl)guanine, sodium salt

To a solution of 0.5 g of sodium metabisulfite in 2 ml of water was added 134 mg (0.5 mmole) of hydrated 4-(guanin-9-yl)-3-oxabutanal. The mixture was warmed just to the point at which a clear solution was obtained (about 50°–60°) and maintained there for 20 minutes. Then the solution was cooled, resulting in immediate crystallization. After standing, the solid was collected on a filter and washed with small volumes of cold water. The product became somewhat gummy but resolidified on trituration with acetone. After prolonged air drying, 110 mg of white solid was obtained, m.p. not less than 350° (darkened beginning at about 250° without melting). NMR (D$_2$O) was consistent with the assigned structure.

| Anal. (C$_8$H$_{10}$N$_5$N$_a$S 1.5 H$_2$O) | | |
|---|---|---|
| | Calculated[a] | Found |
| C | 25.76 | 25.74 |
| H | 3.51 | 3.55 |
| N | 18.78 | 18.88 |
| S | 8.60 | 8.66 |

[a] Calculated for 95% (C$_8$H$_{10}$N$_5$NaO$_6$S 1.5 H$_2$O) contaminated with 5% non-CHNS-containing inorganic impurity.

EXAMPLE 5

9-(3-Phosphono-1-propoxymethyl)guanine

The title compound was prepared by a route patterned after that used by G. H. Jones and J. G. Moffatt [J. Am. Chem. Soc., 90, 5337 (1968)] for the synthesis of 6'-deoxyhomonucleoside-6'-phosphonic acids from nucleoside-5'-carboxaldehydes.

STEP A: Diphenyl 3-[(guanin-9-yl)methoxy]-1-propene-1-phosphonate

To a solution of 1.88 g (3.7 mmole) of diphenyl[(triphenylphosphoranylidene)methyl]phosphonate [J. G. Moffatt and G. H. Jones, U.S. Pat. No. 3,662,031 (1972)] in 18.5 ml of dry DMF stirred in an oil bath at 65°–70° under nitrogen was added in small portions 992 mg (3.7 mmole) of hydrated 4-(guanin-9-yl)-3-oxabutanal over a period of approximately 5 hours. After completion of the addition, the resulting solution was stirred for a further 15 hours at 65°–70°, then cooled, and concentrated by rotary evaporation (at a pressure less than or equal to 2 mm) to give a light amber, viscous syrup. This material was chromatographed on a silica gel column packed in methylene chloride, using a gradient elution with methylene chloride containing increasing percentages of methanol (0 to 10%). Fractions containing the desired product were combined and concentrated to dryness. The residual solid was taken up in warm methanol, filtered, and reconcentrated. After trituration with ether, the residual solid was collected on a filter, washed with additional ether, and dried to give 1.19 g of white solid, m.p. 178°–184° (softened above 120°). TLC (9:1 CHCl$_3$—MeOH) showed a close pair of spots, and 200 MHz NMR (DMSO-d$_6$) was also consistent with a mixture of trans and cis isomers.

STEP B: Diphenyl 3-[(guanin-9-yl)methoxy]propanephosphonate

A mixture of 227 mg (0.5 mmole) of diphenyl 3-[(guanin-9-yl)methoxy]-1-propene-1-phosphonate, 20 mg of platinum oxide, and 10 ml of methanol was shaken with hydrogen (initial pressure 45 psig) on a Parr apparatus. After a few hours, by which time considerable crystallization had occurred, an additional 20 mg of platinum oxide and 15 ml of methanol were added, and the hydrogenation was resumed. After a total of 22 hours, the mixture was heated to dissolve the organic solid and then filtered through Celite. Concentration of the filtrate gave a solid, which was leached with hot acetone, then collected on a filter, and finally washed with acetone and ether. Recrystallization from methanol yielded 105 mg (44%) of white crystals, m.p. 201°–201.5°. Structure and purity were confirmed by TLC (9:1 $CHCl_3$—MeOH) and 200 MHz NMR (DMSO-$d_6$).

| Anal. ($C_{21}H_{22}N_5O_5P$ $H_2O$) | | |
|---|---|---|
| | Calculated | Found |
| C | 53.27 | 52.98 |
| H | 5.11 | 4.88 |
| N | 14.79 | 14.85 |

STEP C: Dibenzyl 3-[(guanin-9-yl)methoxy]propanephosphonate

A mixture of 477 mg (1 mmole) of diphenyl 3-[(guanin-9-yl)methoxy]propanephosphonate and 5.0 ml (5 mmole) of 1.0M sodium benzyloxide in benzyl alcohol (prepared from sodium metal and benzyl alcohol) was stirred under nitrogen at room temperature. All of the solid rapidly dissolved. After 4 hours, the solution was diluted with 125 ml of ether, resulting in heavy precipitation. The mixture was stirred for a few minutes and then filtered. The solid on the filter was washed with ether and then suspended in 50 ml of water. The pH was adjusted to 5–6 with glacial acid, causing the mixture to become fairly thick. After stirring for a few minutes, the solid was collected on a filter, washed with water, and dried to give 371 mg (77%) of white powder, m.p. 140°–143° (preliminary softening). Although this material was indistinguishable from starting material by thin layer chromatography (9:1 $CHCl_3$—MeOH), 200 MHz NMR (DMSO-$d_6$) indicated complete conversion to product. The purity was satisfactory for use in the next step.

STEP D: 9-(3-Phosphono-1-propoxymethyl)guanine

A mixture of 338 mg (0.7 mmole) of dibenzyl 3-[guanin-9-yl)methoxy]propanephosphonate, 140 mg of 20% palladium hydroxide on carbon, and 35 ml of methanol was shaken with hydrogen (initial pressure 43 psig) on a Parr apparatus. After 20 minutes, 35 ml of deionized water was added to dissolve the precipitate, and the hydrogenation was resumed. After a total of 19.5 hours, the mixture was warmed on a steam bath to dissolve additional solid which had precipitated and filtered through Celite. Concentration of the filtrate (finally under high vacuum with mild warming) gave a solid, which was triturated with acetone and then isolated on a filter. Recrystallization from deionized water afforded 142 mg (66%) of white crystals, m.p. 202° decomposes. Structure and purity were confirmed by 200 MHz NMR (DMSO-$d_6$) and analytical high performance liquid chromatography (HPLC) (Micropak AX10 column, gradient elution with 10 mM to 1M potassium dihydrogen phosphate).

| Anal. ($C_9H_{14}N_5O_5P$ 0.25 $H_2O$) | | |
|---|---|---|
| | Calculated | Found |
| C | 35.12 | 35.37 |
| H | 4.75 | 5.12 |
| N | 22.76 | 22.69 |

EXAMPLE 6

Synthesis of 4-(Guanin-9-yl)butanal

STEP A: (±)-3-(2,2-Dimethyl-1,3-dioxolan-4-yl)propyl p-toluenesulfonate

A mixture of 6.44 g (40.5 mmole) of (±)-1,2-O-isopropylidene-1,2,5-pentanetriol [H. Hayashi, K. Nakanishi, C. Brandon, and J. Marmur, *J. Am. Chem. Soc.*, 95, 8749 (1973)], 8.48 g (44.5 mmole) of p-toluenesulfonyl chloride, and 70 ml of dry pyridine was stirred overnight at room temperature under nitrogen. The mixture was poured into about 300 ml of ice-water and extracted with ether. The ether layer was backwashed three times with water, then dried over $MgSO_4$, and filtered. The residue obtained upon concentration of the filtrate was purified by chromatography on a silica gel column (gradient elution with hexane containing 10 to 20% ethyl acetate), yielding 1.96 g (15%) of colorless oil, which was used directly in the next reaction. The structure was confirmed by NMR.

STEP B: (±)-2-Amino-6-benzyloxy-9-[3-(2,2-dimethyl-1,3-dioxolan-4-yl)propyl]purine A solution of 2.41 g (10 mmole) of 2-amino-6-benzyloxypurine [M. J. Robins and R. K. Robins, *J. Org. Chem.*, 24, 2160 (1969)] in 24 ml of dry DMF was treated with 0.44 g (11 mmole) of sodium hydride (60% dispersion in oil). The mixture was stirred under nitrogen as hydrogen was evolved. After gas evolution had ceased and a clear solution had formed, a solution of 3.46 g (11 mmole) of (±)-3-(2,2-dimethyl-1,3-dioxolan-4-yl)propyl p-toluene-sulfonate (prepared as above) in 2 ml of DMF was added. The mixture was stirred at 60° C. for 3 days. The cooled mixture was then neutralized with glacial acetic acid and concentrated in vacuo. The residue was taken up in ethyl acetate, filtered, re-concentrated and chromatographed on silica gel (elution with ethyl acetate). Evaporation of fractions containing clean product gave a residue which, on trituration with ether, yielded 975 mg (25%) of white crystals, mp 111°–112° C. The analytical batch, similarly prepared, had m.p. 115.5°–118°.

| Anal. ($C_{20}H_{25}N_5O_3$) | | |
|---|---|---|
| | Calculated | Found |
| C | 62.65 | 62.50 |
| H | 6.57 | 6.49 |
| N | 18.26 | 18.04 |

STEP C: (±)-9-(4,5-Dihydroxypentyl)guanine

A mixture of 971 mg (2.53 mmole) of (±)-2-amino-6-benzyloxy-9-[3-(2,2-dimethyl-1,3-dioxolan-4-yl)propyl]purine and 8 ml of 1N HCl was stirred at 50° C. for 25 minutes. The mixture was then cooled in ice and adjusted to pH 7 with concentrated ammonium hydroxide, resulting in heavy precipitation. The precipitate was collected on a filter and dried to give 624 mg (97%) of white solid, homogeneous by TLC (silica gel) in 80:20:2 $CHCl_3$—MeOH—$H_2O$, Structure and purity were confirmed by NMR (DMSO-$d_6$). A sample recrystallized from $H_2O$—MeOH had m.p. 211°–213°.

STEP D: 4-(Guanin-9-yl)butanal

To a vigorously stirred solution of 113 mg (0.53 mmole) of sodium periodate in 1.1 ml of $H_2O$ at room temperature was added 101 mg (0.4 mmole) of (±)-9-(4,5-dihydroxypentyl)guanine. After 2 hours, TLC (silica gel, 70:30:3 $CHCl_3$—MeOH—$H_2O$) showed complete conversion to a faster-moving product. The white solid was collected on a filter and washed with some $H_2O$, then with diethyl ether, to give 79 mg of white solid. Recrystallization from $H_2O$—MeOH yielded 29 mg (33%) of white solid, m.p. not less than 300° C. By 200 MHz NMR (DMSO-$d_6$), the material consisted of a mixture of the free aldehyde and the covalent hydrate. A similar preparation showed only the free aldehyde by NMR.

| Anal. ($C_9H_{11}N_5O_2$ 1.87 $H_2O$) | | |
|---|---|---|
| | Calculated | Found |
| C | 42.41 | 42.77 |
| H | 5.83 | 5.61 |
| N | 27.48 | 27.10 |

EXAMPLE 7

| Oil in Water Cream Base | |
|---|---|
| 4-(guanin-9-yl)-3-oxabutanal | 5.0 g |
| Lanolin, Anhydrous | 20.0 g |
| Polysorbate 60 | 4.0 g |
| Sorbitan Monopalmitate | 2.0 g |
| Light Liquid Paraffin | 4.0 g |
| Propylene Glycol | 5.0 g |
| Methyl Hydroxybenzoate | 0.1 g |
| Purified Water | to 100.0 g |

EXAMPLE 8

| Water Soluble Ointment Base | |
|---|---|
| 4-(guanin-9-yl)-3-oxabutanal | 0.5 g |
| Glycerol | 15.0 g |
| Macrogol 300 | 20.0 g |
| Polyethylene Glycol 1500 | 64.5 g |

EXAMPLE 9

| Tablet - (Total weight 359 mg) | |
|---|---|
| 4-(guanin-9-yl)-3-oxabutanal | 100 mg |
| Lactose | 200 mg |
| Starch | 50 mg |
| Polyvinylpyrrolidone | 5 mg |
| Magnesium Stearate | 4 mg |

EXAMPLE 10

Substitute other compounds of the invention (e.g. others of the compounds listed on pages 9 and 10) for 4-(guanin-9-yl)-3-oxabutanal in Examples 7 to 10 to prepare other pharmaceutical compositions of the present invention.

What is claimed is:

1. A compound of the formula:

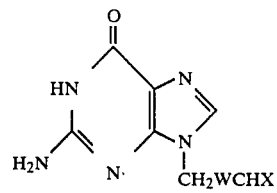

and the pharmaceutically acceptable salts thereof wherein W is —$OCH_2$—, —$CH_2CH_2$—, —$SCH_2$— or —CH=CH—;

X is

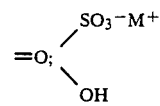

wherein $M^+$ is a pharmaceutically acceptable alkali metal cation; =$NOR^1$; $NR^3$;

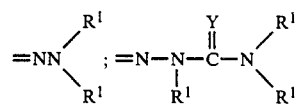

wherein Y is O, S or NH.HA wherein HA is a pharmaceutically acceptable inorganic or organic strong acid;

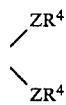

wherein each Z is independently O, S or $NR^1$ and $R^4$ is $R^2$ or the two $R^4$s taken together with the Z moieties to which they are attached form a group

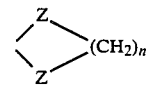

wherein n is 2 or 3;

each $R^1$ is independently hydrogen, alkyl having 1 to 6 carbon atoms, phenyl, phenyl substituted with halo, with alkyl having 1 to 4 carbon atoms or with alkoxy having 1 to 4 carbon atoms, phenylalkyl wherein the alkyl moiety has 1 to 4 carbon atoms, or

each $R^2$ is independently alkyl having 1 to 6 carbon atoms, phenylalkyl wherein the alkyl moiety has 1 to 4 carbon atoms, phenyl, phenyl substituted with halo, with alkyl having 1 to 4 carbon atoms or with alkoxy having 1 to 4 carbon atoms;

each $R^3$ is independently selected from phenyl, phenyl substituted with halo, phenyl substituted with alkyl having 1 to 4 carbon atoms or phenyl substituted with alkoxy having 1 to 4 carbon atoms.

2. A compound according to claim 1, wherein W is —OCH2— or —CH2CH2— and X is as defined in claim 1.

3. A compound according to claim 2, wherein X is

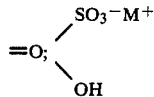

wherein M+ is a pharmaceutically-acceptable alkali metal cation; =NOR¹; =NR³;

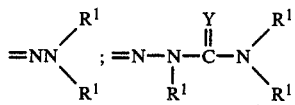

wherein Y is O or NH.HA wherein HA is hydrochloric acid, formic acid or phosphoric acid; inorganic or organic strong acid;

wherein each Z is independently O, S or NR¹ and R⁴ is R² or the two R⁴s taken together with the Z moieties to which they are attached form a group

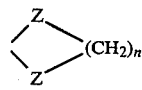

wherein n is 2 or 3;
each R¹ is independently hydrogen, alkyl having 1 to 6 carbon atoms, phenyl, phenyl substituted with halo, phenyl substituted with alkyl having 1 to 4 carbon atoms, phenyl substituted with alkoxy having 1 to 4 carbon atoms, phenylalkyl wherein the alkyl moiety has 1 to 4 carbon atoms, or

each R² is independently alkyl having 1 to 6 carbon atoms, phenylalkyl wherein the alkyl moiety has 1 to 4 carbon atoms, phenyl, phenyl substituted with halo, with alkyl having 1 to 4 carbon atoms or with alkoxy having 1 to 4 carbon atoms;
each R³ is selected from phenyl, phenyl substituted with halo, phenyl substituted with alkyl having 1 to 4 carbon atoms or phenyl substituted with alkoxy having 1 to 4 carbon atoms.

4. A compound according to claim 3, wherein X is

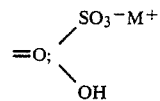

wherein M+ is a pharmaceutically-acceptable alkali metal cation; =NOR¹;

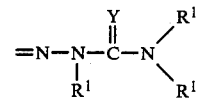

wherein Y is O or NH.HA wherein HA is hydrochloric acid, formic acid or phosphoric acid;

wherein each Z is independently O or NR¹ and R⁴ is alkyl of 1 to 6 carbon atoms or alkoxyalkyl of 1 to 6 carbon atoms or the two R⁴s taken together with the Z moieties to which they are attached form a group

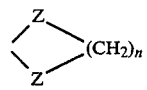

wherein Z is S, O or NR¹ and n is 2 or 3;
each R¹ is independently hydrogen, alkyl having 1 to 6 carbon atoms, phenyl, phenyl substituted with halo, phenyl substituted with alkyl having 1 to 4 carbon atoms, phenyl substituted with alkoxy having 1 to 4 carbon atoms, phenylalkyl wherein the alkyl moiety has 1 to 4 carbon atoms, or

each R² is independently alkyl having 1 to 6 carbon atoms, phenylalkyl wherein the alkyl moiety has 1 to 4 carbon atoms, phenyl or phenyl substituted with halo, with alkyl having 1 to 4 carbon atoms or with alkoxy having 1 to 4 carbon atoms;
each R³ is selected from phenyl, phenyl substituted with halo, phenyl substituted with alkyl having 1 to 4 carbon atoms or phenyl substituted with alkoxy having 1 to 4 carbon atoms.

5. 4-(Guanin-9-yl)-3-oxabutanal, according to claim 1.

6. 4-(Guanin-9-yl)butanal, according to claim 1.

7. An antiviral pharmaceutical composition comprising an effective amount of a compound according to claim 1 and a pharmaceutically-acceptable carrier.

8. A method of treating viral infections in mammals, birds or fish comprising administering an effective amount of a compound according to claim 1.

* * * * *